United States Patent [19]
Goldstein et al.

[11] Patent Number: 4,798,744
[45] Date of Patent: Jan. 17, 1989

[54] FIXATION OF POLYMERS RETAINING LIQUIDS IN A POROUS STRUCTURE

[75] Inventors: Guy Goldstein, Colmar; Michel Pierre, Mulhouse, both of France

[73] Assignee: Beghin-Say S.A., Thumeries, France

[21] Appl. No.: 44,500

[22] PCT Filed: Jul. 22, 1986

[86] PCT No.: PCT/FR86/00257

§ 371 Date: Mar. 23, 1987

§ 102(e) Date: Mar. 23, 1987

[87] PCT Pub. No.: WO87/00438

PCT Pub. Date: Jan. 29, 1987

[30] Foreign Application Priority Data

Jul. 23, 1985 [FR] France ................................ 85 11256

[51] Int. Cl.$^4$ .............................................. B05D 3/02
[52] U.S. Cl. ................................ 427/389.9; 427/391; 427/392
[58] Field of Search ..................... 427/389.9, 391, 392; 428/289, 290

[56] References Cited

U.S. PATENT DOCUMENTS 4,059,552 11/1977 Zweigle et al. ................. 128/284 X
4,235,237 11/1980 Mesek et al. ........................ 128/284

FOREIGN PATENT DOCUMENTS 0036463 9/1981 European Pat. Off. .
0077510 4/1983 European Pat. Off. .
2083487 3/1982 United Kingdom .

Primary Examiner—Thurman K. Page
Attorney, Agent, or Firm—A. W. Breiner

[57] ABSTRACT

The process applies to polymers obtained by a water-in-oil process, that is to say, a reverse emulsion process or a suspension process in reversible phase. The process of fixation of this type of polymer in or on a porous support is characterized in that it comprises the impregnation of the porous support with said reverse suspension or emulsion resulting from the polymerization reaction and the removal of solvent from the support. By said process, complexes are obtained which present improved absorption properties and offer a better holding of the product to the support.

6 Claims, No Drawings

FIXATION OF POLYMERS RETAINING LIQUIDS IN A POROUS STRUCTURE

This invention relates to a process for the fixation of polymers retaining liquids inside a support with an open porous structure, as well as to the complex obtained by this process.

Polymers retaining liquids are insoluble hydrophilic macromolecules capable of forming a gel in the presence of a liquid. They are called improved retention additives (abbreviated as IRA), hydrogels, hydroretainers and superabsorbents. The best known products are alginates, for example those sold under the trade name CECALGUM, cross-linked carboxymethylcellulose (trade name AKUCELL of ENKA-AKZO), grafted starches (trade name SANWET of SANYO CHEMICAL), synthetic derivatives of the acrylamide type (trade name AQUASORB of FLOERGER) or acrylate type (trade names AQUAUKEEP of SEITETSU, AQUALIC of NIPPON SHOKUBAI or ARASORB of ARAKAWA).

Numerous processes exist for fixing powder on or in a support. The powder can be bonded to the support by passing steam, as described in patent FR No. 2,066,324. A deposit of polymer can also be fixed by spraying latex (patent FR No. 2,402,474), or else held in a tangle of fibres (patent FR No. 2,446,357).

The polymer can be deposited on fibres by oiling (patent FR No. 2,283,255), on non-woven material (patent EP No. 72569) or in a foam.

The polymer can be formed directly on the support (patent EP No. 123,500. Polymerization is effected by electron-bombardment of the monomers deposited on the support. It is obtained in a very short time, limiting the formation of long macromolecular chains. According to the patent cited above, the polymer obtained after electron-bombardment of monomers has a salt-water absorption capacity of about 10 ml/g. For this reason, the complex obtained, to be very absorbent, must contain a large quantity of this polymer, between 3 and 12 times its own weight.

In the same field, patent application JP No. 5,884,804 describes a method for the polymerization of a mixture of monomers impregnated in a porous support. However, the polymerization time is long, limiting production capacity. In addition, the polymerization reaction is carried out at a high temperature, making it necessary to select supports stable at these temperatures.

According to another method described in patent GB No. 2,084,487, particles of a superabsorbent polymer are immobilized on a porous support by suspending the particles of the polymer, initially in a dry state, in an organic solvent, and then applying the suspension in the form of a liquid film to the support and, finally, removing the solvent by drying. In U.S. Pat. No. 4,235,237, the polymer particles are swollen and suspended in water and then applied to the support.

The object of the invention is to provide a new, simple to use method for the deposition of superabsorbent polymers onto a support, yielding a complex with improved properties.

The polymers covered by the invention are polymers obtained by a water-in-oil process. It relates to a reverse emulsion or suspension process in reversible phase. In processes of this type, the aqueous phase contains the monomers and is dispersed in a continuous oil phase, that is, a solvent not miscible with water, by means of one or several surfactants generally of more lipophilic than hydrophilic character. Surfactants of non-ionic character, like sorbitan esters, are used preferentially.

According to the reverse emulsion process, the polymerization initiator is generally a peroxide soluble in the solvent, as described in patent DE No. 1,089,173.

According to the suspension processes in reversible phase, the polymerization initiator, which is generally a persulfate, is contained in the aqueous phase. This is described, for example, in patent EP No. 36,463 for the manufacture of superabsorbent products known under the trade name AQUAKEEP or in patent DE No. 3,331,644 for the manufacture of a superabsorbent product sold under the trade name of KAO SOAP.

After the reaction, the polymer obtained is found to be dispersed in the solvent in the continuous phase. The solvent is generally a cyclic or cyclic saturated hydrocarbon in a proportion of 5 to 50% by weight, more precisely between 10 and 25%. Cyclohexane or heptane are preferentially used as solvent. After extraction and drying, a polymer is obtained which is in the form of a powder whose principal property is that it is very absorbent.

In the process according to the invention, use is made of the reverse emulsion or suspension containing the polymer obtained after the polymerization reaction. The process is characterized in that it consists in impregnating the porous support with said reverse emulsion or suspension of polymer resulting from the polymerization reaction and removal of the solvent from the support.

By impregnation is understood the action of making the support imbibe the emulsion or suspension, whether this be by padding, by coating, by filtration, by projection, by spraying, or by any other equivalent technique.

By removal of the solvent is understood any action which allows the solvent to be separated from the porous support and the polymer. Operations such as dewatering, drying, evaporation under partial vacuum can be used alone or in conjunction or even simultaneously.

The polymers according to the invention are deposited in the support, before having been subjected to any drying operations, that is, preferentially immediately after, or a short time after manufacture, this characteristic being contrary to patent GB No. 2,083,487 in which the solid polymer is resuspended in an organic solvent and U.S. Pat. No. 4,235,237 in which the solid polymer is inflation with water and applied to the support.

Impregnation is effected on a porous support, which can be non-woven material, paper, fibre pile or a foam. The choice of a support must be guided in particular by its porosity, preferably greater than 0.5. Thus the polymer micelles in suspension or emulsion in a solvent migrate into the pores if their diameter is less than that of the pores. The advantage of using the suspension or emulsion during or preferentially at the end of the polmerization resides in the fact that the micelles are microscopic. Their size is generally less than 100 microns. It is even considered that each micelle consists of a single hydrophilic macromolecule, like a ball of wool. These micelles, whose size is more precisely of the order of a few tens of microns or less are able to migrate into the very fine pores such as those provided by compacted structures of cellulose fibres. A very wide choice therefore is available. Furthermore, depending on whether a very open porous support or a very close support is considered, the size of the micelles can be increased or decreased by agitating or not agitating the emulsion or suspension by varying the quantity of surfactant present in the emulsion or else suspension or by causing flocculation to take place, for example, by changing the viscosity of the solvent-polymer mixture. In the latter case, the addition of water may suffice. Moreover, by destabilizing the emulsion or suspension, the addition of water promotes the precipitation of the polymer. This operation is then performed preferentially before impregnation by adding water to the support.

Thus the invention comes to separating the polymer from the solvent by entraining the non-dried polymer by means of a porous support. This latter retains polymers to a lesser or greater extent so that the concentration of polymers in the liquid being imbibed by the support is greater after impregnation than that of the emulsion or suspension before impregnation.

If the polymer micelles are of a size that is too large compared with that of the support, they do not penetrate the support. The polymer is deposited essentially on the surface without being appreciably fixed to the support. This phenomenon is covering when a solid polymer is suspended in a solvent, as for example in patent GB No. 2,083,487. Thus the solid obtained by a water-in-oil process results in the coalescence of the micelles. The particles obtained thereby are always of a grain size greater than that of the micelles. As regards the solids obtained by grinding, they generally contain few fine particles of less than 100 microns. Sieving, a costly operation, is required to be able to incorporate a powder in a solvent medium in a support whose pores are fine.

The invention is illustrated by the examples reported hereinunder:

the polymer used is an alkaline acrylate polymer obtained by the method described in patent EP 36,463 in reverse suspension in cyclohexane containing 15% non-volatile matter.

the method used for the determination of retention, hereinafter referred to as R30, is described as follows:

Retention is measured by placing a sample of 0.5 g in an 8 g sanitary towel. The towel containing the sample under pressure of 2.5 kPa. The very high, apparent viscosity was about 0.97. The R30 retention of this support alone was practically nil: 0.02 g/g.

A second support consisted of a non-woven material sold under the trade name HOLNEST made by BEGHIN-SAY, composed of an ester fibre pile (trade name Hétérofil made by ICI) of 20 g/m$^2$ thermo-softened by calendering giving a diamond pattern. Its density was 7 cm$^3$/g. The void volume is about 6 cm$^3$/g or an apparent porosity of 0.85. The R30 retention of this support alone was about 0.04 g/g.

A third support consisted of a product based on cellulose fibre (85%) obtained by the dry route, reinforced by spraying latex (15% dry) onto the two faces. Of a grammage of 95 g/m$^2$, with a density of 5 to 12 cm$^3$/g according to the areas, this wiping product made by BEGHIN-SAY had a total porosity comparable to that the non-woven HOLNEST. However, the pores were smaller as the number of fibres per unit volume was very much higher. This support was less permeable than the preceding ones with polymer grains to be deposited. The R30 retention was about 1.5 g/g.

EXAMPLE 1

The polymer suspension mentioned above was prepared in a tank into which the carded ouatine pile was immersed. After impregnation, the pile was removed and dried. Table 1 summarizes the results obtained depending on whether the pile was dried horizontally on a teflon plate (line a and b) or vertically (line c), or else whether the support had previously been impregnated with solvent (line d) or water (line e, at a rate of 21%, line f, at a rate of 31%).

The columns in the table give the weight of the support alone, dry or wet in the case of pre-impregnation, the weight of the complex obtained after impregnation and drying, the weight in grams of the dry IRA fixed on the support after impregnation, and compared with the support alone (X), and finally the R30 retention as measured for the complex on the one hand, reduced to the IRA contained in the complex, on the other hand.

TABLE 1

| OPERATING CONDITIONS | SUPPORT | | COMPLEX | IRA | | R30 RETENTION | |
|---|---|---|---|---|---|---|---|
| | | | | WEIGHT | | COMPLEXE | IRA |
| Examples 1 | DRY | WET | (DRY) | m (g) | X | (g/g) | (g/g) |
| Dry PET carded pile | | | • | | | | |
| Horizontal drying | | | | | | | |
| a | 1.11 g | | 8.87 g | 7.76 g | X 7 | 15 | 17 |
| b | 1.16 g | | 8.78 g | 7.62 g | X 6.5 | 15 | 17 |
| Vertical drying | | | | | | | |
| c | 2.05 g | | 11.25 g | 10.20 g | X 5 | 13 | 14.5 |
| Pile + cyclohexane | 0.93 g | 1.03 g (11%) | 5.30 g | 4.37 g | X 4.5 | 13.5 | 16 |
| Pile + water | | | | | | | |
| e | 0.78 g | 0.99 g (21%) | 4.30 g | 3.52 g | X 4.5 | 13 | 16 |
| f | 0.89 g | 1.17 g (31%) | 6.70 g | 5.81 g | X 6.5 | 14.5 | 17 | of powder is immersed in salt water containing 10 g of sodium chloride per liter for 30 minutes. It is then centrifuged at 1250 G for one minute. By comparison and difference between a towel with a sample and one without a sample, the retention of salt water per gram of polymer sample is evalutated. The retention, measured by this method, of the polymer selected for the tests is between 42 ml and 62 ml/g.

Tests have been performed on three types of different supports.

The first support consisted of thermo-softened 65 g/m$^2$ polyester fiber pile, of density of about 35 g/m$^3$ It is seen therefore that according to this method, the complex retained more than 10 times, between 13 and 15 times, its own weight of water.

EXAMPLE 2

The same suspension was used for the impregnation of non-woven material (trade name Holnest) described above.

This support is less porous than ouatine; it was found that the deposit of improved retention additive (IRA) was less: 3 to 4 g/g. By humidifying the non-woven material before impregnation a slightly greater amount of IRA (line b) was fixed than in the absence of water (line a in table 2).

g/g (4f) in accordance with the amount of IRA deposited. Water impregnation (4a, 4b, 4c, 4d, 4e) was used to increase the precipitation of the polymer onto the support by destabilizing the polymer in reverse suspension.

TABLE 2

| OPERATING CONDITIONS Examples 2 | SUPPORT DRY | SUPPORT WET | COMPLEX (DRY) | IRA WEIGHT m (g) | X | R30 RETENTION COMPLEX (g/g) | R30 RETENTION IRA (g/g) |
|---|---|---|---|---|---|---|---|
| NT Holnest dry a | 0.27 | | 1.10 g | 0.83 g | X 3.1 | 14.5 | 19 |
| NT Holnest + water b | 0.59 | 1.43 g (42%) | 2.84 g | 2.25 g | X 3.8 | 14.5 | 18 |

EXAMPLE 3

Another polymer suspension was prepared, still according to the same reverse suspension process, the parameters being chosen to obtain a polymer with better properties than those of examples 1 and 2.

The tests were performed on 5 cm machine width ouatine samples. The samples were unwound from a perforated cylinder rotating in a 100 ml tank.

It was found that the amount of polymer deposited was less since the micelles in suspension were smaller.

It was found that the optimum quantity of water to wet the polyester support was then between 50 and 100%. Beyond this, a significant difference was no longer obtained. By entraining more polymer, the emulsion or suspension became exhausted.

The man versed in the art seeks to obtain a best final product from a very fine emulsions and suspensions destabilized in supports that are very porous but have a large specific area so as to divide the polymer as finely as possible.

TABLE 4

| TESTS | SUPPORT DRY (g) | SUPPORT WET (g) (% H$_2$O) | SUPPORT IMPREGNATED (g) | COMPLEX DRY (g) | IRA m (g) | IRA X | R30 RETENTION (g/g) COMPLEX | R30 RETENTION (g/g) IRA |
|---|---|---|---|---|---|---|---|---|
| a | 1.34 | 1.47 (10) | 16.0 | 4.47 | 3.13 | 2.3 | 22 | 31.5 |
| b | 1.50 | 1.87 (24) | 20.9 | 5.65 | 4.15 | 2.8 | 22 | 30 |
| c | 1.59 | 2.29 (44) | 37.3 | 8.55 | 6.96 | 4.4 | 21.5 | 26.5 |
| d | 1.64 | 6.2 (338) | 39.5 | 10.40 | 8.76 | 5.3 | 20.5 | 24 |
| e | 1.35 | 5.7 (320) | 31.0 | 7.73 | 6.38 | 4.7 | 15.7 | 19.0 |
| f | 1.36 | 7.2 (430) | 34.5 | 7.40 | 6.04 | 4.4 | 15 | 18.4 |
| g | 1.22 | 6.4 (420) | 33.8 | 7.70 | 6.48 | 5.3 | 17 | 20.2 |
| h | 1.24 | 7.2 (480) | 25.6 | 5.33 | 4.09 | 3.3 | 16.3 | 21.2 |

With an amount of IRA of 1 to 2.5 g/g deposited and a complex retention of 20 ml/g, the R30 retention of the IRA was estimated at between 25 and 40 g/g. See table 3.

TABLE 3

| TEST(N) 5 × 40 cm | SUPPORT (g) | IMPREGNATED SUPPORT g | IMPREGNATED SUPPORT X | COMPLEX (g) | IRA/SUPPORT m(g) | IRA/SUPPORT X | R30 RETENTIONS Complex | R30 RETENTIONS IRA |
|---|---|---|---|---|---|---|---|---|
| a | 1.35 | 12.8 | 8.5 | 2.90 | 1.55 | 1.1 | 21.3 | 40 |
| b | 1.25 | 12.9 | 9.3 | 3.20 | 1.95 | 1.6 | 20.3 | 33 |
| c | 1.30 | 16.6 | 11.7 | 4.57 | 3.27 | 2.5 | 20.7 | 29 |
| d | 1.20 | 13.6 | 10.3 | 3.06 | 1.86 | 1.5 | 15 | 25 |
| e | 1.30 | 13.7 | 9.5 | 3.64 | 2.34 | 1.8 | 17.5 | 27 |
| f | 1.40 | 12.9 | 8.2 | 3.09 | 1.69 | 1.2 | 16 | 29 |
| g | 1.30 | 12.9 | 8.9 | 3.57 | 2.27 | 1.7 | 18 | 28 |

EXAMPLE 4

The same suspension as in Example 3 was used.

The ouatine was pre-impregnated with water. The quantity of IRA deposited increased with the quantity of water being imbibed by the polyester pile. The performance levels of the IRA fell from 40 g/g (3a) to 17

EXAMPLE 5

Another reverse suspension of sodium acrylate in cyclohexane, stabilized with the same quantity of surfactant as before, was prepared.

Part of it was used to impregnate the ouatine, another part was used to obtain 90 g of solid polymer whose particles were very fine. The mean grain size was 100 microns. The R30 retention was 45 to 52 g/g.

Three types of tests were performed, the results being given in Table 5.

TABLE 5

| TEST | SUPPORT DRY (g) | SUPPORT WET (g) | IMPREGNATED SUPPORT (g) | COMPLEX DRY (g) * | COMPLEX DRY (g) ** | IRA/SUPPORT (g) * | IRA/SUPPORT (g) ** | RETENTION COMPLEX** ·g/g |
|---|---|---|---|---|---|---|---|---|
| 5a A | 0.35 | | 3.27 | 0.89–0.88 | | 0.54–0.53 | | 25 |
| B | 0.36 | | 3.25 | 0.89–0.72 | | 0.53–0.36 | | 23 |
| C | 0.36 | | 3.56 | 0.89–0.97 | | 0.53–0.61 | | 26 |
| 5b D | 0.37 | | 2.75 | 0.89–0.45 | | 0.52–0.08 | | 4 |

TABLE 5-continued

| TEST | SUPPORT DRY (g) | SUPPORT WET (g) | IMPREGNATED SUPPORT (g) | COMPLEX DRY (g) * | COMPLEX DRY (g) ** | IRA/SUPPORT (g) * | IRA/SUPPORT (g) ** | RETENTION COMPLEX** g/g |
|---|---|---|---|---|---|---|---|---|
| E | 0.33 | | 3.03 | 1.20 | 0.59 | 0.87 | 0.26 | 18 |
| F | 0.38 | | 2.48 | 0.60 | 0.47 | 0.22 | 0.09 | 5 |
| G | 0.30 | | 1.66 | 0.50 | 0.39 | 0.20 | 0.09 | 6 |
| H | 0.36 | | 2.64 | 0.68 | 0.49 | 0.32 | 0.13 | 7 |
| I | 0.30 | | 1.66 | 0.41 | 0.40 | 0.11 | 0.10 | 7 |
| 5c J | | 0.34–0.75 | 3.06 | 0.67 | 0.59 | 0.33 | 0.25 | 21 |
| K | | 0.38–0.77 | 3.61 | 0.81 | 0.73 | 0.43 | 0.35 | 16 |
| L | | 0.39–0.90 | 4.88 | 1.11 | 0.68 | 0.72 | 0.29 | 20 |

*After drying
**After drying and manipulation of samples, that is, before analysis.

tests 5a

The ouatine was impregnated with the reverse suspension.

Complexes A, B and C contained 1.5 g of polymer per gram of ouatine, distributed inside the ouatine. They retained 23 to 26 grams of synthetic urine per gram of complex. The polymer deposited retained about 40 to 45 g/g. It was deposited and fixed in the ouatine. Manipulating the sample did not cause any loss of non-fixed polymer.

test 5b 40 g of solid polymer obtained were suspened in 225 g of cyclohexane under reflux at a temperature of 50° C. containing the same surfactant in the same proportion as that specified during its synthesis. The suspension was particularly unstable. The ouatine samples also were impregnated with the suspension while being agitated. After drying, it was found that the polymer was not very well fixed to this very porous support. The polymer was deposited in the ouatine cells. It was not fixed as shown by the losses in weight between the weighings before analysis and those after drying (third and fourth column in table 5). This process, different from that claimed, was less efficient.

The retentions of complexes D to I were small as the quantity of polymer present at the time of analysis was minute.

tests 5c

In contrast to tests 5b, the ouatine was wetted with water (about 100% water) before being immersed in the suspension. The solid polymer was fixed better, the losses smaller. The quality of the complex (smaller retentions) was lower, but its cost due to drying of polymer and then the complex was higher than that obtained in example 5a according to the invention.

EXAMPLE 6

The porous support used was the product mentioned above obtained by the dry method. The pores of this support were narrower than those of the ouatine.

Three types of tests were performed, the results being given in Table 6.

tests 6a

This support immersed in the reverse suspension as in tests 5a became imbibed with it. The complex before analysis (**) was heavier as it contained 8% water compared with the complex weighed after drying (*). As shown in samples A, B, C and D, there was no loss of polymer. This polymer was well fixed to the support.

Polymer retention was about 40 to 50 g/g, as in Example 5a.

These examples, 5a and 6a, illustrate the invention well.

TABLE 6

| TESTS | SUPPORT DRY (g) | IMPREGNATED SUPPORT | COMPLEX DRY (g) * | COMPLEX DRY (g) ** | IRA/SUPPORT ** | RETENTION COMPLEX ** |
|---|---|---|---|---|---|---|
| 6a A | 0.48 | 4.70 | 0.84 | 0.99 | 0.51 | 20 g/g |
| B | 0.44 | 4.51 | 0.86 | 0.93 | 0.49 | 20 |
| C | 0.42 | 4.51 | 0.84 | 0.90 | 0.48 | 25 |
| D | 0.44 | 4.62 | 0.90 | 0.97 | 0.53 | 22 |
| 6b E | 0.44 | 4.14 | 0.83 | 0.68 | 0.24 | 13 |
| F | 0.45 | 4.05 | 0.89 | 0.87 | 0.42 | 18 |
| G | 0.45 | 3.99 | 0.84 | 0.76 | 0.31 | 14 |
| H | 0.43 | 3.90 | 0.87 | 0.81 | 0.38 | 16 |
| I | 0.43 | 4.19 | 0.80 | 0.65 | 0.22 | 14 |
| J | 0.42 | 3.50 | 0.63 | 0.63 | 0.21 | 14 |
| 6c K | 0.42 | 4.58 | 0.77 | 0.77 | 0.35 | 22 |
| L | 0.45 | 5.16 | 0.99 | 0.95 | 0.50 | 20 |
| M | 0.46 | 5.51 | 1.00 | 0.98 | 0.52 | 20 |
| N | 0.47 | 4.26 | 0.62 | 0.62 | 0.15 | 8 |
| O | 0.44 | 5.95 | 1.22 | 1.30 | 0.66 | 19 |
| P | 0.44 | 6.68 | 1.49 | 1.67 | 1.25 | 21 |

*After drying
**Before analysis tests 6b

The support was impregnated with the suspension of example 5d. The deposit of polymer was equivalent. However, it was found that the powder was deposited on the surface in the form of a crust, which disintegrated when the complex was manipulated.

In this support, less porous than the ouatine, the resuspended polymer practically no longer penetrated, as was seen with samples E, G, H, I, J tests 6c The support was impregnated with the suspension of example 5b in which 40 g of cyclohexane were replaced by 40 g of water. The fixation of polymer was satisfactory as the slightly gelled polymer adhered to the support. But the swollen polymer practically did not penetrate this support which was less porous than the ouatine. An examination of samples K, L, M, N, O and P showed that it had definitely remained on the surface.

Suspending a solid polymer in a carrier solvent followed by impregnation of a porous support and finally removing the solvent are known operations. (5a, 5c, 6b, 6c). However, they do not allow the preparation of complexes of such good quality as the process claims, in which the polymer which has never been dried is separated from the solvent while it is contained in the porous support. The product obtained was characterized in that it comprised at least 0.45 gram of insoluble, hydrophilic polymer per gram of support. Its R30 retention was at least equal to 10 ml per gram of product.

What is clamed is:

1. A process for the deposition and fixation of insoluble hydrophilic polymers in or on a porous support, said polymers being obtained according to a "water-in-oil" reverse emulsion or suspension process comprising impregnating the porous support with said reverse emulsion in the liquid state as it is recovered from the polymerization reaction, and thereafter removing the suspending solvent from the support.

2. A process according to claim 1, wherein the reverse emulsion or suspension is destabilized during the impregnation in order to facilitate the deposition of the polymer on the porous support.

3. A process according to claim 2, wherein the reverse emulsion or suspension is destabilized by addition of water during impregnation.

4. A process according to claim 3, wherein the destabilizing water is added by impregnation of the porous support before its impregnation with the reverse emulsion or suspension.

5. A process according to claim 1, wherein the reverse emulsion or suspension includes between 10% and 30% of a hydrophilic polymer.

6. A process according to claim 1, wherein the porous support is a non-woven material, paper, a pad of bonded or unbonded cellulose and/or synthetic fibers, characterized in that the porosity of said support is greater than 0.5.

* * * * *